(12) United States Patent
Allred et al.

(10) Patent No.: US 7,980,698 B2
(45) Date of Patent: Jul. 19, 2011

(54) POWER-ADJUSTED ABERROMETER

(75) Inventors: Lloyd G. Allred, Bountiful, UT (US); Jeffrey B. McBeth, Rochester, NY (US); Barry Eagan, Spencerport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 56 days.

(21) Appl. No.: 12/273,720

(22) Filed: Nov. 19, 2008

(65) Prior Publication Data
US 2010/0123874 A1    May 20, 2010

(51) Int. Cl.
*A61B 3/00* (2006.01)
*A61B 3/10* (2006.01)

(52) U.S. Cl. ........................................ 351/246; 351/221
(58) Field of Classification Search .................... 351/221
See application file for complete search history.

(56) References Cited

U.S. PATENT DOCUMENTS

| | | | |
|---|---|---|---|
| 4,029,396 A | 6/1977 | Shenker |
| 4,190,332 A | 2/1980 | Body |
| 4,471,448 A | 9/1984 | Williams |
| 4,490,039 A | 12/1984 | Bruckler |
| 5,062,702 A | 11/1991 | Bille |
| 5,382,988 A | 1/1995 | Nanjo |
| 5,504,543 A | 4/1996 | Ueno |
| 5,523,809 A | 6/1996 | Kohayakawa |
| 5,537,163 A | 7/1996 | Ueno |
| 5,684,561 A | 11/1997 | Yancey |
| 5,777,719 A | 7/1998 | Williams |
| 5,891,132 A | 4/1999 | Hohla |
| 5,949,521 A | 9/1999 | Williams |
| 5,963,300 A | 10/1999 | Horwitz |
| 6,042,233 A | 3/2000 | Mihashi |
| 6,086,204 A | 7/2000 | Magnante |
| 6,130,419 A | 10/2000 | Neal |
| 6,155,684 A | 12/2000 | Bille |
| 6,199,986 B1 | 3/2001 | Williams |
| 6,234,978 B1 | 5/2001 | Mihashi |

(Continued)

FOREIGN PATENT DOCUMENTS

DE    42 22 395 A1    7/1992

(Continued)

OTHER PUBLICATIONS

International Search Report (PCT/ISA/210) and Written Opinion (PCT/ISA/237) mailed on Jan. 25, 2010.

(Continued)

*Primary Examiner* — Jordan M. Schwartz
(74) *Attorney, Agent, or Firm* — Jeffrey B. Powers

(57) ABSTRACT

Aspects of the invention are directed to apparatus and methods for automatically setting a power level of light emitted by a light source; illuminating a retina of a patient with the light emitted by the light source; receiving, at a sensor, light reflected from the retina of the patient; providing a signal based upon the received light; determining whether the signal meets one or more signal quality criteria; automatically setting a second power level of light emitted by the light source; and repeating the steps of illuminating the patient's eye, receiving reflected light, providing the signal, and determining whether the signal meets the signal quality criteria. In some embodiments, setting the second power level is performed in response to determining whether the signal meets the signal criteria. In still other embodiments, the method comprises selecting an operating power based upon the signal quality criteria.

28 Claims, 7 Drawing Sheets

U.S. PATENT DOCUMENTS

| | | |
|---|---|---|
| 6,264,328 B1 | 7/2001 | Williams |
| 6,271,914 B1 | 8/2001 | Frey |
| 6,271,915 B1 | 8/2001 | Frey |
| 6,299,311 B1 | 10/2001 | Williams |
| 6,304,723 B1 | 10/2001 | Kohayakawa |
| 6,460,997 B1 | 10/2002 | Frey |
| 6,497,483 B2 | 12/2002 | Frey |
| 6,511,180 B2 | 1/2003 | Guirao |
| 6,550,917 B1 | 4/2003 | Neal |
| 6,598,973 B2 | 7/2003 | Campin |
| 6,649,895 B1 | 11/2003 | Wirth |
| 6,656,209 B1 | 12/2003 | Ginsburg |
| 6,736,509 B2 | 5/2004 | Martino |
| 6,739,721 B2 | 5/2004 | Altmann |
| 6,827,444 B2 | 12/2004 | Williams |
| 7,036,934 B1 | 5/2006 | Youssefi |
| 7,044,603 B2 | 5/2006 | Yoon |
| 7,335,867 B2 | 2/2008 | Topa |
| 2003/0009156 A1 | 1/2003 | Levine |
| 2003/0086063 A1 | 5/2003 | Williams |
| 2003/0142271 A1 | 7/2003 | Ross |
| 2004/0233388 A1* | 11/2004 | Artsyukhovich et al. ..... 351/216 |
| 2005/0099824 A1* | 5/2005 | Dowling et al. .............. 362/572 |
| 2005/0225725 A1 | 10/2005 | Warden |
| 2006/0126019 A1 | 6/2006 | Liang |
| 2007/0159600 A1* | 7/2007 | Gil et al. ....................... 351/221 |
| 2008/0278683 A1 | 11/2008 | Su |
| 2009/0226052 A1* | 9/2009 | Fedele et al. .................. 382/125 |

FOREIGN PATENT DOCUMENTS

| | | |
|---|---|---|
| DE | 42 22 395 A1 | 1/1994 |
| EP | 0 910 984 A | 4/1999 |
| JP | 11 137522 A | 5/1999 |
| WO | WO 93/014470 A1 | 7/1993 |
| WO | WO 93/024048 A | 12/1993 |
| WO | WO 96/000031 A1 | 1/1996 |
| WO | WO 99/027334 A1 | 6/1999 |
| WO | WO 01/028476 A1 | 4/2001 |
| WO | WO 2001/28410 A1 | 4/2001 |

OTHER PUBLICATIONS

Weeks, Arthur R., Jr., *Transforms Used in Electronic Image Processing*, p. 71 and *Spatial Filtering*, p. 129-144, Fundamentals of Electronic Image Processing (SPIE/IEEE Series on Imaging Science and Engineering) (1996).

Johnsonbaugh, et al., Chapter 7: *Processing of Waveforms and Images*, Pattern Recognition and Image Analysis, Prentice Hall PTR, pp. 293-296, 308 (1996).

Liang et al., *Objective Measurement of Wave Aberrations of the human eye with the use of a Hartmann-Shack wave-front sensor*, J. Opt. Soc. Am. A., vol. 11, No. 7, pp. 1949-1957 (Jul. 1994).

Witthoft, C., *Wavefront Sensor Noise Reduction and Dynamic Range Expansion by means of Optical Image Intensification*, Optical Engineering, Soc. of Photo-Optical Instrumentation Engineers, vol. 29, No. 10, Oct. 1990, pp. 1233-1238.

Liang, et al, *Aberrations and retinal image quality of the normal human eye*, Journal of the Optical Society of America, vol. 14, No. 11, Nov. 1997, pp. 2873-2883.

\* cited by examiner

POWER-ADJUSTED ABERROMETER

FIELD OF INVENTION

The present invention relates to ophthalmological instruments, and more particularly to aberrometers having automated power adjustment.

BACKGROUND

Accurate characterization of wavefronts produced by an eye is desirable in the field of ophthalmology to facilitate correction of an eye's image-forming system through surgery and/or corrective lens fabrication.

Although various types of aberration measurement apparatus (hereinafter, "aberrometers") are known, Hartmann-Shack type aberrometers are widely used in commercial ophthalmic applications. FIG. 1 is a simplified schematic illustration of an example of a Hartmann Shack aberrometer 100.

In use, a beam of light from a light source 110 in the aberrometer is directed toward the cornea C of an eye E and onto the retina R by beam splitter 120. The light reflects from the retina and is projected through the cornea, and forms an aberrated wavefront. The aberrated wavefront reenters the aberrometer, and is incident on an array of lenslets 130. The light forms an array of spots $d_{1l}$-$d_{1n}$ on sensor 140. The locations of the spots relative to the locations that spots would have occupied in the absence of wavefront aberrations provides data that is used to characterize the wavefront and thus detect aberrations. FIG. 2 is a graphical illustration of example intensity values on a representative area of sensor 140 (including a plurality of spots $d_{i,j}$).

A seminal reference in the field of ophthalmic wavefront detection is Liang et al., *Objective measurement of wave aberrations of the human eye with the use of a Hartmann-Shack wave-front sensor*, Journal of the Optical Society of America, Vol. 11, No. 7, pp. 1-9 (July 1994), the disclosure of which is hereby incorporated by reference in its entirety. Improvements to the technique of Liang et al., id., are taught in Liang and Williams, *Aberrations and retinal image quality of the normal human eye*, Journal of the Optical Society of America, Vol. 4, No. 11, pp. 2873-2883 (November 1997), and in Williams et al. U.S. Pat. No. 5,777,719, the disclosures of which are hereby incorporated by reference in their entireties.

The ability to accurately measure aberrations and use the measurement information in corrective applications depends on the ability to precisely determine the location of the centers of the spots associated with each lenslet in an array. An inability to accurately detect the centers of all image spots frustrates the characterization of the wave aberrations and subsequent procedures that rely upon those characterizations.

Typically, center coordinates $c_x$, $c_y$ of an image spot are calculated by centroid calculation (i.e., summation of weighted values of the incident light intensity $I(x_i, y_i)$ at points $(x_i, y_i)$ on sensor 140). Many factors can operate to frustrate accurate centroid determination. One such factor is attenuation of the light as it passes through portions of the patient's eye. The cornea and lens of the eye tend to become more and more opaque with age. The light can also be severely attenuated by the presence of cataracts. FIG. 3 illustrates an exemplary image of aberrometer detector output for a normal eye, while FIG. 4 illustrates an exemplary image of aberrometer detector output for the eye of a cataract patient. As a result of attenuation of light passing through the cataract, image spots in the affected region are very faint and may be barely detectable or completely undetectable. The result of such attenuation is that the center coordinates of the corresponding image spots cannot be determined with desired accuracy, yielding unsatisfactory measurements of aberration in the eyes of afflicted patients.

SUMMARY

Aspects of the present invention are directed to automatic adjustment and selection of an appropriate light level in an aberrometer based upon the quality of the data obtained at different light levels. Some embodiments and some advantages of those embodiments are summarized here. Other embodiments and advantages may not be explicitly set forth.

An aspect of the invention is directed to a method comprising automatically setting a power level of light emitted by a light source; illuminating a retina of a patient with the light emitted by the light source; receiving, at a sensor, light reflected from the retina of the patient; providing a signal based upon the received light; determining whether the signal meets one or more signal quality criteria; automatically setting a second power level of light emitted by the light source; and repeating illuminating the patient's eye, receiving reflected light, providing the signal, and determining whether the signal meets the signal quality criteria. Advantages of this aspect include facilitating the collection of optical data at an adequate power level which is determined and set automatically rather than manually.

In some embodiments, setting the second power level is performed in response to determining whether the signal meets the signal criteria. In still other embodiments, the method comprises selecting an operating power based upon the signal quality criteria. Advantages of these embodiments may include making power level selection an objective, free from the subjective influence of a human technician, helping to ensure that an adequate image is obtained of every patient's eye.

In some embodiments, the method comprises repeating the steps of illuminating the patient's eye, receiving reflected light, providing the signal, and determining whether the signal meets the signal quality criteria until the signal meets the one or more signal quality criteria. Advantages of these embodiments may include a relatively quick and objective power level selection process that stops when the signal quality is adequate.

In some embodiments, the method comprises identifying a plurality of peak signal levels within the signal; determining a number of peak signal levels that are not less than a predetermined value; and determining whether the number is not less than a predetermined number. Advantages of these embodiments may include a relatively quick processing of the received signal, one that may permit evaluating the signal quality without requiring full analysis of the received signal.

In some embodiments, the method comprises identifying a plurality of peak signal levels within the signal; identifying a background signal level; determining a number of peak signal levels that exceed the background signal level by at least a predetermined value; and determining whether the number is not less than a predetermined number. Advantages of these embodiments may include a relatively quick processing of the received signal, one that may permit evaluating the signal quality without requiring full analysis of the received signal. Additional advantages may include the aspect that peak signal over background is, in some applications, a particularly useful and relevant measure of signal quality.

In some embodiments, the method comprises identifying a plurality of peak signal levels within the signal; determining a number of peak signal levels that that fall between a first predetermined value and a second predetermined value; and determining whether the number is not less than a predetermined number. Advantages of these embodiments may include a relatively quick processing of the received signal, one that may permit evaluating the signal quality without requiring full analysis of the received signal. Additional advantages can include permitting the selection of a preferred or optimal range of peak signal levels.

In some embodiments, the method comprises identifying a plurality of peak signal levels within the signal; identifying a background signal level; determining, for each of the plurality of peak signal levels, a signal-to-noise ratio; determining a number of signal-to-noise ratios that are not less than a predetermined value; and determining whether the number is not less than a predetermined number. Advantages of these embodiments may include a relatively quick processing of the received signal, one that may permit evaluating the signal quality without requiring full analysis of the received signal. Additional advantages may include the aspect that signal-to-noise ratio is, in some applications, a particularly useful and relevant measure of signal quality.

In some embodiments, signal comprises a plurality of signal levels, and the method comprises generating a histogram of at least a portion of the plurality of signal levels; identifying, in the histogram, a peak corresponding to a subset of the plurality of the signal levels comprising signal levels distinguishable from a background signal level; and determining whether a number of signal levels in the peak is not less than a predetermined value. Advantages of these embodiments may include the aspect that a histogram is an efficient way to get an overall picture of certain characteristics of a dataset without requiring a relatively lengthy detailed analysis of the data.

In some embodiments, the sensor comprises a plurality of elements; and the signal comprises a plurality of signal levels, each signal level corresponding to one of the plurality of elements of the sensor. The method further comprises determining, for each of the plurality of sensor elements, whether a signal at the sensor element is saturated; determining a number of sensor elements at which the signal at the sensor element is saturated; and determining whether the number is not greater than a predetermined number. Advantages of these embodiments may include the aspect that it relates signal quality directly to the number of saturated peaks. Too many saturated peaks can distort the optical measurement being taken, and also may indicate that the overall light level illuminating the patient is undesirably high.

In some embodiments, the method comprises generating a Fourier transform of at least a portion of the signal; determining a signal-to-noise ratio of at least a portion of the Fourier transform of the signal; and determining whether the signal-to-noise ratios is not less than a predetermined value. Advantages of these embodiments may include analyzing the signal quality relatively quickly without the need for a full analysis of the signal.

In some embodiments, the sensor comprises an array of sensor elements. The method further comprises receiving at the array of sensor elements light reflected from the retina of the patient through an array of lenslets and generating a signal indicative of the optical power received at each of the sensor elements of the array of sensor elements. Advantages of these embodiments may include the advantages of using techniques associated with lenslet arrays for evaluating optical properties of the patient's eye.

In further embodiments, the method comprises determining a plurality of center positions in the signal, each center position corresponding to one of the lenslets in the array of lenslets; determining an uncertainty in the center position for each of the plurality of center positions; determining a number of center positions having uncertainties that are not greater than a predetermined uncertainty value; and determining whether the number is not less than a predetermined number. Advantages of these embodiments may include the aspect of relating signal quality directly to the precision with which the center of each peak can be determined, which in some applications can be a key parameter in obtaining a useful measurement of the optical properties of the patient's eye.

In some embodiments, the method comprises setting a power control signal of the light source. Advantages of these embodiments may include making power level selection an objective, free from the subjective influence of a human technician, helping to ensure that an adequate image is obtained of every patient's eye. In still further embodiments, the method comprises setting the power control signal of the light source by pulse-width modulation. Advantages of these embodiments may include the aspect that that pulse-width modulation is a straightforward and reliable way of setting the power of a light source with an electrical control signal.

In some embodiments, the method comprises setting the attenuation of a filter in a beam path of the light emitted by the light source. Advantages of these embodiments may include the aspect that filters can be provided with arbitrary gradation to achieve whatever granularity of control is desired for a particular application.

Another aspect of the invention is directed to an apparatus comprising a light source adapted to illuminate a patient's retina; a sensor adapted to receive light reflected from the patient's retina and to provide a signal based upon the received light; and a processor coupled to the sensor. The processor is adapted to set a first power level of light emitted by the light source; receive the signal provided by the sensor; process the signal to determine whether the signal meets one or more signal quality criteria; set a second power level of light emitted by the light source; and repeat receiving the signal and processing the signal.

In some embodiments, the processor is adapted to set the second power level in response to determining whether the signal meets one or more signal criteria. In some embodiments, the processor is adapted to repeat receiving the signal and processing the signal until the signal meets the one or more signal quality criteria. In further embodiments, the processor is adapted to select an operating power based upon the signal quality criteria. Advantages of these embodiments may include making power level selection an objective, free from the subjective influence of a human technician, helping to ensure that an adequate image is obtained of every patient's eye.

In some embodiments, the processor is further adapted to identify a plurality of peak signal levels within the signal; determine a number of peak signal levels that are not less than a predetermined value; and determine whether the number is not less than a predetermined number. Advantages of these embodiments may include a relatively quick processing of the received signal, one that may permit evaluating the signal quality without requiring full analysis of the received signal.

In some embodiments, the processor is further adapted to identify a plurality of peak signal levels within the signal; identify a background signal level; determine a number of peak signal levels that exceed the background signal level by at least a predetermined value; and determine whether the number is not less than a predetermined number. Advantages of these embodiments may include a relatively quick processing of the received signal, one that may permit evaluating the signal quality without requiring full analysis of the received signal. Additional advantages may include the aspect that peak signal over background is, in some applications, a particularly useful and relevant measure of signal quality.

In some embodiments, the processor is further adapted to identify a plurality of peak signal levels within the signal; determine a number of peak signal levels that fall between a first predetermined value and a second predetermined value; and determine whether the number is not less than a predetermined number.

In some embodiments, the processor is further adapted to identify a plurality of peak signal levels within the signal; identify a background signal level; determine, for each of the plurality of peak signal levels, a signal-to-noise ratio; determine a number of signal-to-noise ratios that are not less than a predetermined value; and determine whether the number is not less than a predetermined number. Advantages of these embodiments may include a relatively quick processing of the received signal, one that may permit evaluating the signal quality without requiring full analysis of the received signal. Additional advantages can include permitting the selection of a preferred or optimal range of peak signal levels.

In some embodiments, the signal comprises a plurality of signal levels. The processor is further adapted to generate a histogram of at least a portion of the plurality of signal levels; identify, in the histogram, a peak corresponding to a subset of the plurality of the signal levels comprising signal levels distinguishable from a background signal level; and determine whether a number of signal levels in the peak is not less than a predetermined value. Advantages of these embodiments may include the aspect that a histogram is an efficient way to get an overall picture of certain characteristics of a dataset without requiring a relatively lengthy detailed analysis of the data.

In some embodiments, the sensor comprises a plurality of elements and the signal comprises a plurality of signal levels, each signal level corresponding to one of the plurality of elements of the sensor. The processor is further adapted to determine, for each of the plurality of sensor elements, whether a signal at the sensor element is saturated; determine a number of sensor elements at which the signal at the sensor element is saturated; and determine whether the number is not greater than a predetermined number. Advantages of these embodiments may include the aspect that it relates signal quality directly to the number of saturated peaks. Too many saturated peaks can distort the optical measurement being taken, and also may indicate that the overall light level illuminating the patient is undesirably high.

In some embodiments, the processor is further adapted to generate a Fourier transform of at least a portion of the signal; determining a signal-to-noise ratio of at least a portion of the Fourier transform of the signal; and determining whether the signal-to-noise ratios is not less than a predetermined value. Advantages of these embodiments may include analyzing the signal quality relatively quickly without the need for a full analysis of the signal.

In some embodiments, the apparatus further comprises an array of lenslets and the sensor comprises an array of sensor elements. The sensor is further adapted to receive the light reflected from the patient's retina through an array of lenslets, and the signal based upon the received light is indicative of the optical power received at each of the sensor elements of the array of sensor elements. Advantages of these embodiments may include the advantages of using techniques associated with lenslet arrays for evaluating optical properties of the patient's eye.

In further embodiments, the processor is adapted to determine a plurality of center positions in the signal, each center position corresponding to one of the lenslets in the array of lenslets; determine an uncertainty in the center position for each of the plurality of center positions; determine a number of center positions having uncertainties that are not greater than a predetermined uncertainty value; and determine whether the number is not less than a predetermined number. Advantages of these embodiments may include the aspect of relating signal quality directly to the precision with which the center of each peak can be determined, which in some applications can be a key parameter in obtaining a useful measurement of the optical properties of the patient's eye.

In some embodiments, the processor is adapted to set a power control signal of the light source. Advantages of these embodiments may include making power level selection an objective, free from the subjective influence of a human technician, helping to ensure that an adequate image is obtained of every patient's eye. In further embodiments, the processor is adapted to set the power control signal of the light source by pulse-width modulation. Advantages of these embodiments may include the aspect that that pulse-width modulation is a straightforward and reliable way of setting the power of a light source with an electrical control signal. In further embodiments, the processor is adapted to set the attenuation of a filter in a beam path of the light emitted by the light source. Advantages of these embodiments may include the aspect that filters can be provided with arbitrary gradation to achieve whatever granularity of control is desired for a particular application.

Still further embodiments include other combinations of the functionality and/or features of embodiments particularly described herein.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Definitions

Figure 1:
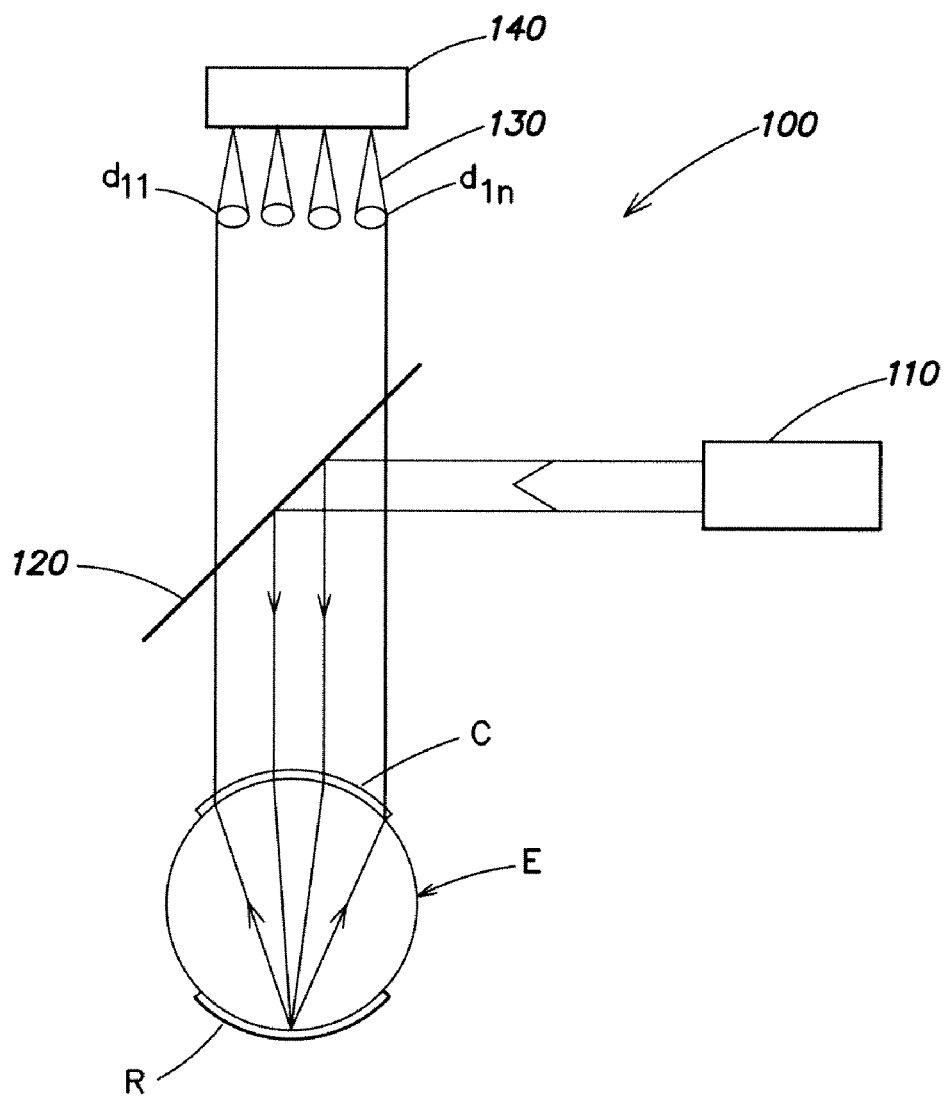
FIG. 1 is a simplified schematic illustration of a Hartmann Shack aberrometer projecting light onto an eye and producing a plurality of spots on a sensor.

For convenience, before further description of the invention, certain terms employed in the specification and claims are collected here.

Between: As used in the claims, "determining whether X is between A and B" includes embodiments in which the endpoints are included as well as embodiments in which the endpoints are excluded.

"Is not less than" includes embodiments in which the test is whether A>B as well as embodiments in which the test is whether A≧B.

"Is not greater than" includes embodiments in which the test is whether A<B as well as embodiments in which the test is whether A≦B.

"Peak signal level" means a signal level representing a local maximum in a signal describing a distribution of light levels in space, such as a signal from an array of sensor elements. For example, in embodiments, a signal from an array of sensor elements (or from any subset of an array of sensor elements) may be represented as a collection of dots or local signal peaks (such as the signal represented in FIG. 3 discussed further below). A "peak signal level" is a signal value representing the strength of one such local signal peak. In embodiments, a peak signal level may be the local maximum signal in a single element in an array of sensor elements. In other embodiments the peak signal level may be a spatially averaged or summed signal, such that the peak signal level actually contains contributions from more than one element of the array. A peak signal level is representative of the strength of the signal in a local peak, however determined or defined.

"Power level" is radiant intensity (or any other measure of light power or intensity) measured at the light source, at the output of the instrument, or at any point along the light path.

A "row" of lenslets or sensor elements means any line of lenslets in an array of lenslets or sensor elements, whether oriented as a row or a column.

A "sensor" is any optical detector or array of optical detectors (sensor elements) for producing an electrical signal (either digital or analog) indicative of the properties of incident light (for example, optical power and/or spatial distribution of optical power).

"Signal quality criteria" means any criteria by which it can be determined whether a signal is adequate or optimized; some examples of signal quality criteria are discussed with more specificity below.

Overview of Certain Embodiments

Aspects of the present invention are directed towards methods for automatically setting a power level of light emitted by the light source of an aberrometer and selecting a suitable power level for measuring the aberration in a patient's eye based upon the quality of the data collected by the aberrometer. Where the quality of an aberrometer signal is compromised, for example by losses of light incurred passing through a cataract or other opacified region of the patient's eye, increasing the intensity of the light from the aberrometer's light source can improve the signal quality. Requiring technicians to manually adjust the light levels, however, presents potential concerns of safety and repeatability. Additionally, a light level selected for one patient may not be appropriate for a subsequent patient. Further, relying on the subjective judgment of a technician as to the appropriate light level for any patient can result in images with inadequate data.

In embodiments of the present invention, the method comprises automatically setting a power level of light emitted by the light source and illuminating the retina of a patient with light emitted by the light source. For example, the light level may be set automatically as a result of a processor executing an instruction, as discussed below. Light reflected from the retina is captured at a sensor, a signal is generated based upon the light received at the sensor. This signal is processed to determine whether it meets one or more signal quality criteria. A new power level is automatically set, and the retina again illuminated. A signal is generated at the new power level, and this new signal is also processed to determine whether it meets the signal criteria.

Figure 5:
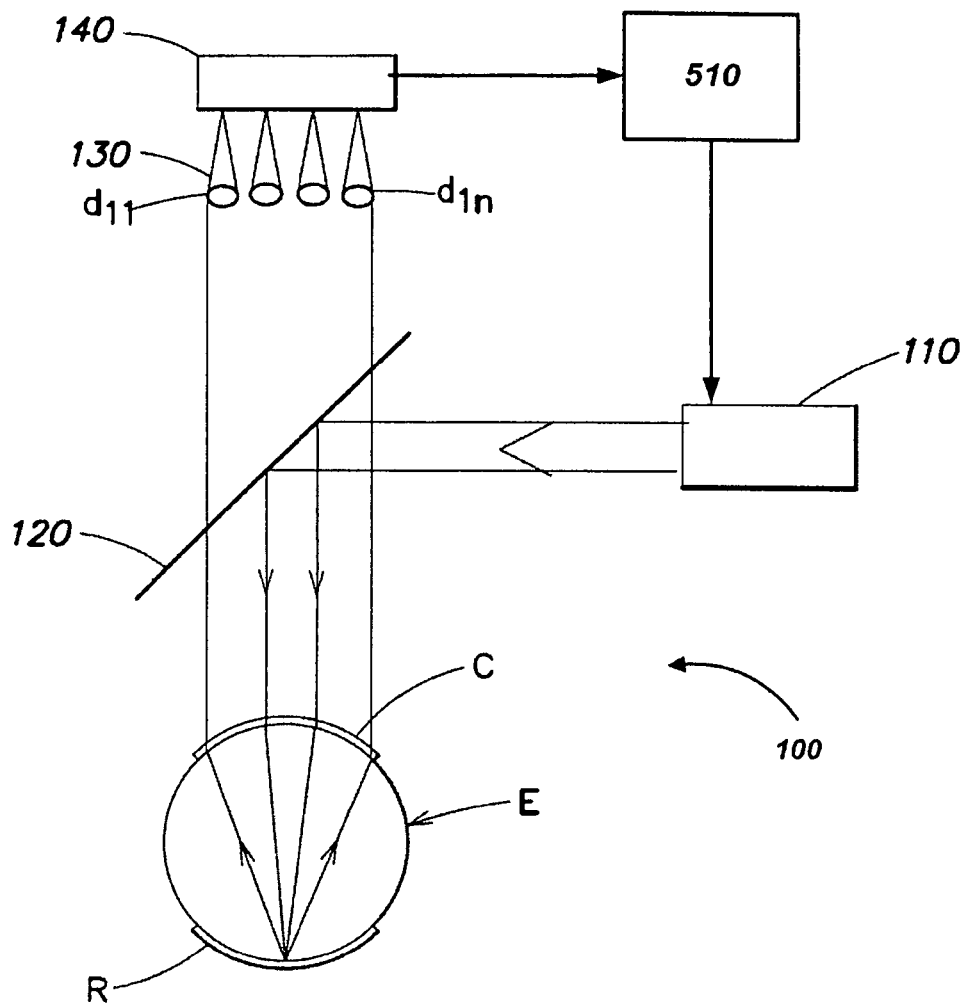
FIG. 5 is a simplified schematic illustration of a Hartmann Shack aberrometer as described herein.

An aberrometer according to an embodiment of the present invention is schematically illustrated in FIG. 5. As discussed above in connection with FIG. 1, light source 110 emits light that is directed into the patient's eye by splitter 120. Light reflected from the patient's retina R passes through splitter 120 and impinges on lenslet array 130, where it is focused into spots at sensor 140.

In embodiments of the present invention, aberrometer 100 also includes processor 510. Processor 510 may include one or more microprocessors, central processing units (CPUs), computing devices, microcontrollers, digital signal processors, application-specific integrated circuits, or like devices, or any combination thereof. Typically, a processor 510 will receive instructions (e.g., from a memory or like device), and execute those instructions, thereby performing one or more processes defined by those instructions. In embodiments of the present invention, the action of processor 510 executing an instruction automatically sets the power level of the light source 110. Processor 510 also receives the signal from sensor 140 and processes that signal to determine whether it meets predefined signal quality criteria.

In some embodiments, the steps of setting a power level, illuminating the patient's retina, receiving reflected light, and processing the signal are repeated, at different power levels, until the signal quality criteria are satisfied. For example, the processor may be programmed to begin at a low power level and increase the power level incrementally until it reaches a power level at which the signal quality criteria are satisfied. This power level may then be used to measure aberration in the patient's lens. In embodiments, the processor is programmed to set a new power level in response to determining that the signal fails to meet the signal quality criteria.

Figure 6:
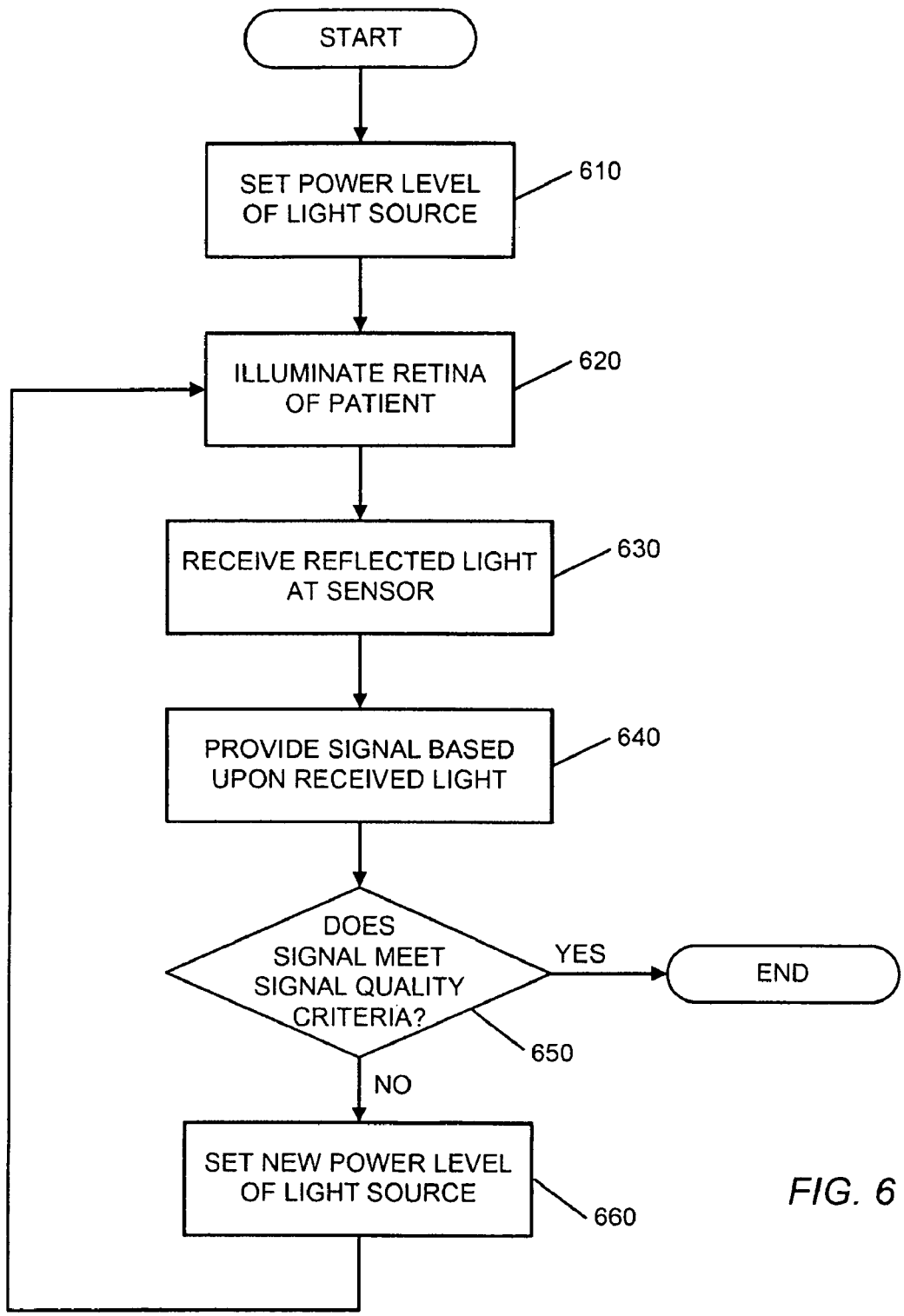
FIG. 6 is a flow chart of an embodiment of a method according to the present invention.

The flow chart FIG. 6 illustrates an example of an embodiment of a method according to the present invention. At step 610, the power level of the light source is set, for example, by the processor executing an instruction and providing a control signal to the light source. At step 620, light from the light source is permitted to illuminate the retina of the patient as illustrated in FIG. 5. At step 630, light reflected from the patient's retina is received at a sensor such as sensor 140. As noted above, in the aberrometer illustrated in FIG. 5, the light is permitted to pass through lenslet array 130 before being received at sensor 140, so that the light received at sensor 140 forms a pattern of spots on the sensor. At step 640, a signal is provided (for example, by sensor 140 to processor 510) based upon the light received at the sensor.

At step 650, the signal is processed (as discussed further below) to determine whether the signal meets some predefined signal quality criteria. In the embodiment illustrated in FIG. 6, if the signal meets the signal quality criteria the method is complete, and the aberration measurement may proceed at the current power level of the light source. If the signal does not meet the signal quality criteria, a new power level is set (step 660) and the steps of illuminating the patient's eye (620), receiving light reflected from the patient's eye (630), providing a signal based upon the received light (640), and determining whether the signal quality criteria are met (650) are repeated. In embodiments these steps 660 and 620-650 may be repeated until a power level is found at which the signal quality criteria are satisfied. The power level that satisfies the signal quality criteria may then be used to perform the aberration measurement.

In still other embodiments, the processor is programmed to step through a predetermined sequence of power levels, receiving and storing (for example, in volatile memory or on a hard disk) a signal at each power level in the sequence. In such embodiments, the processor may process the stored signal data after stepping through the sequence of power levels, and select a power level that satisfies the signal quality criteria. This power level may then be used to measure aberration in the patient's lens.

Figure 7:
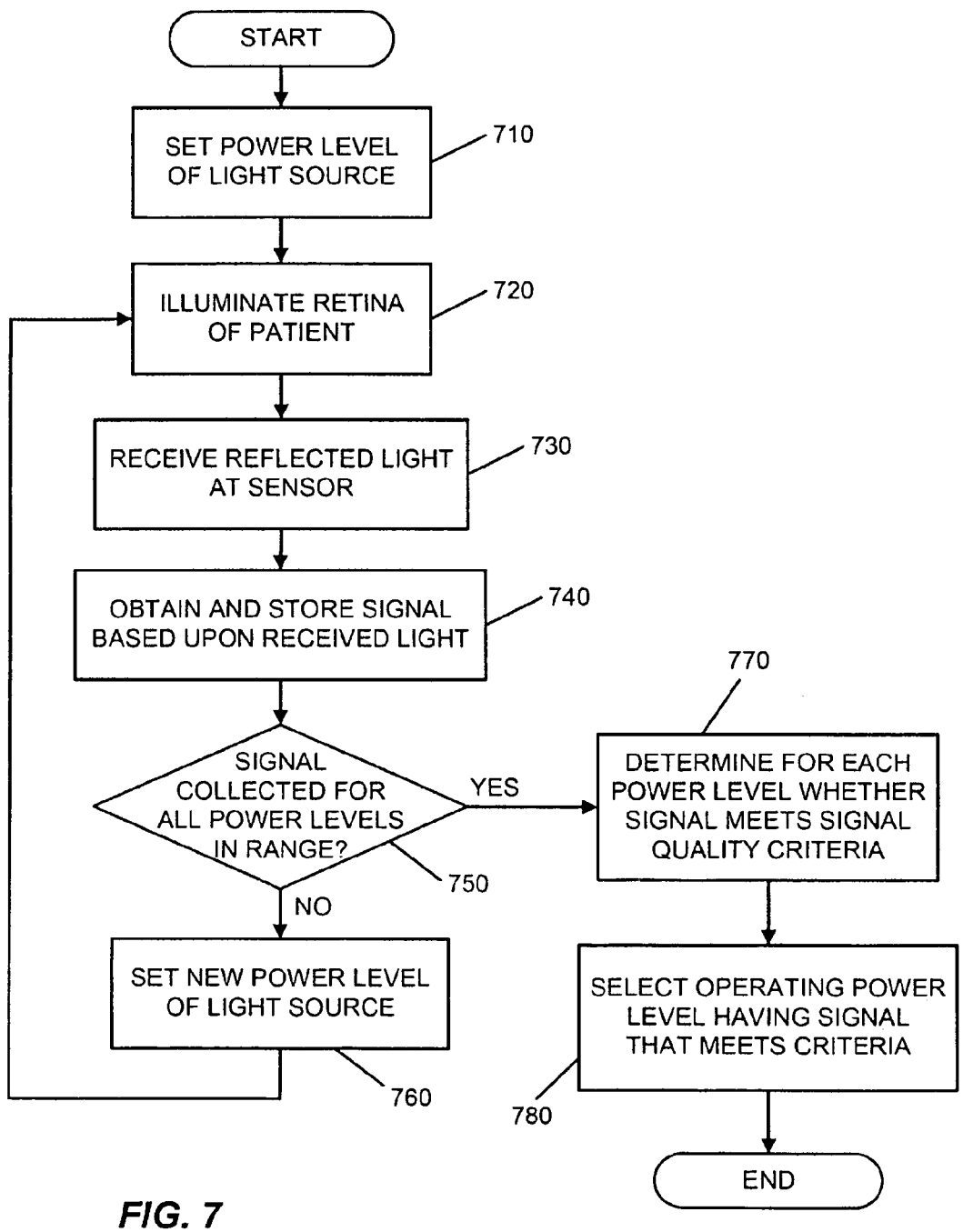
FIG. 7 is a flow chart of an embodiment of a method according to the present invention.

An example of such an embodiment is illustrated in the flow chart of FIG. 7. At step 710, the power level of the light source is set as in the embodiment illustrated in FIG. 6. The patient's retina is illuminated at step 720. At step 730, light reflected from the patient's retina is received at the sensor. At step 740, a signal is obtained based upon the light received at the sensor. This signal is stored by the processor, for example in volatile memory or on a storage medium such as a hard drive.

In the embodiment illustrated in FIG. 7, the processor is instructed to step through a predetermined selection of power level settings (for example, by incrementing by a fixed amount from a minimum setting to a maximum setting) and to store signal data for each of these power level settings. Thus, at step 750, the processor determines whether signal data has been collected for every power level setting. If it has not, a new power level is set (step 760), and the steps of illuminating the patient's eye (720), receiving light reflected from the patient's eye (730), and obtaining and storing a signal based upon the received light (740) are repeated.

Once a signal has been collected for all desired power levels, the stored signals are each processed (as discussed further below) to determine whether each signal meets the predefined signal quality criteria (step 770). In step 780, an operating power is selected from the power levels whose signals do meet the signal quality criteria. For example, the lowest power level that yields an adequate signal may be chosen. The selected power level may then be used to perform the aberration measurement.

Determining Whether Signal Quality Criteria are Satisfied

There are a variety of suitable signal quality criteria that can be applied to determine whether the signal is adequate for the aberration measurement. Any suitable method of analyzing signal quality criteria may be employed with the systems and methods of the present invention.

Figure 2:
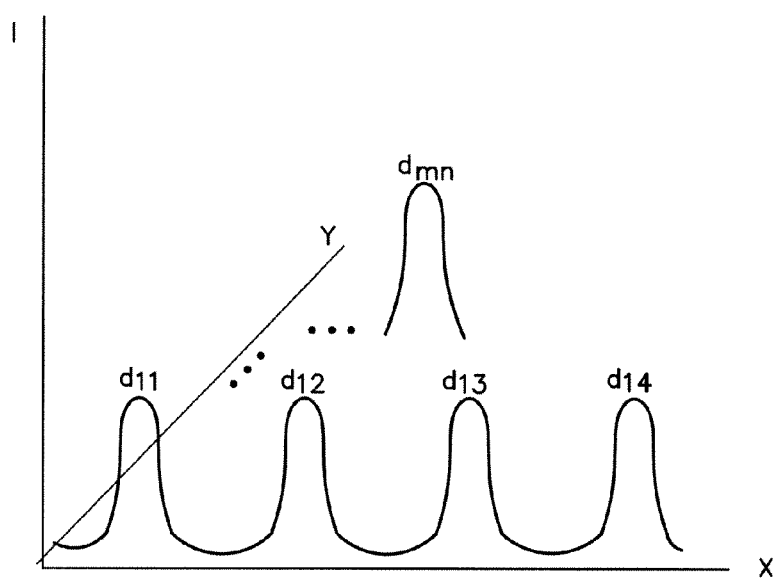
FIG. 2 is a schematic illustration of example intensity values on a representative area of the sensor in the aberrometer shown in FIG. 1.
Figure 3:
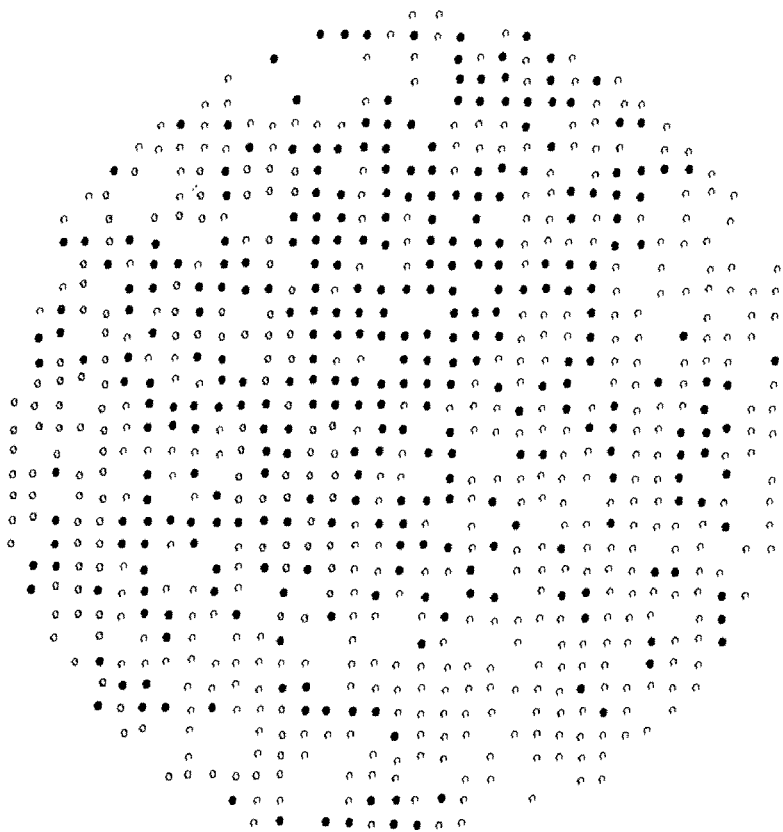
FIG. 3 is an example of sensor output obtained by illuminating a normal eye with an aberrometer.
Figure 4:
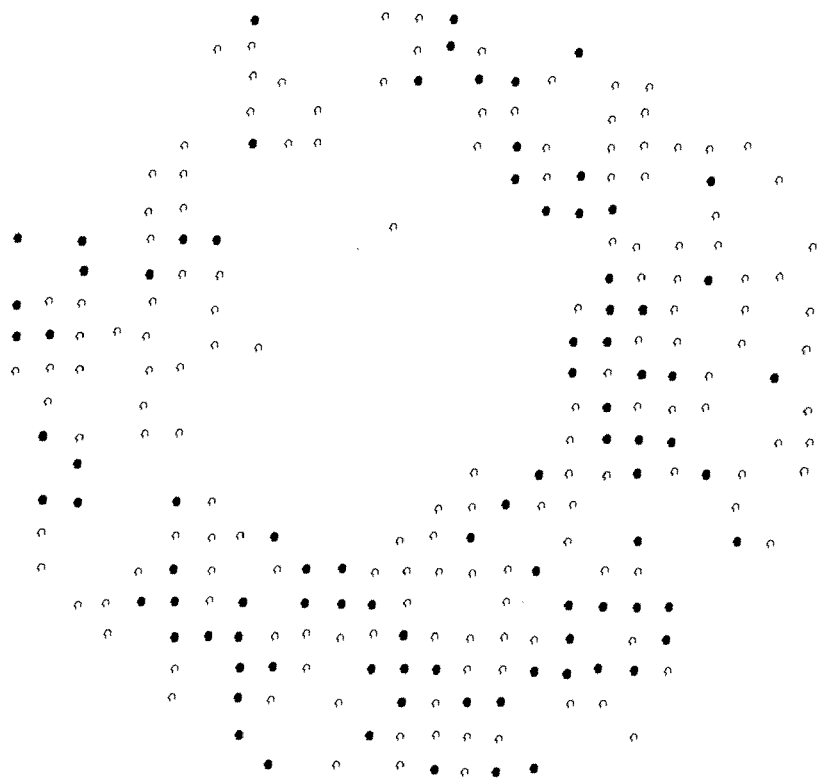
FIG. 4 is an example of a sensor output obtained by illuminating the eye of a cataract patient with an aberrometer.

Generally, the signal comprises a number of light level peaks corresponding to the lenslets 130, as illustrated in FIGS. 2, 3, and 4. As discussed above, where the light is attenuated by a cataract or other opacity in the patient's eye, the light level peaks may be too small for adequate determination of the center position of the peaks. On the other hand, where the light level is too high, the elements of sensor 140 may saturate, which also introduces uncertainty into the determination of the center position. Because of variation in opacity across different light paths through the patient's eye, the signal will generally include a number of peaks with relatively low light levels and a number of peaks with relatively high light levels.

Thus, in some embodiments, the signal quality criteria may be defined as a number of peaks having light levels that fall in an acceptable range, i.e., above a minimum light level threshold and below a maximum light level threshold. The minimum light level threshold may be, for example, the lowest peak light level that yields an acceptable determination of the peak's center position. The maximum light level threshold may be, for example, a light level associated with a saturated element of sensor 140, or a light level slightly below that at which the elements of sensor 140 become saturated.

In such embodiments, the processor analyzes the signal to identify a peak signal corresponding to each lenslet in the array of lenslets 130 (or, alternatively, a peak signal corresponding to each lenslet in a subset of the lenslets in the array, such as a single row or column of lenslets in the array, or a set of lenslets corresponding to a region of particular interest in the patient's eye), and counts the number of peak signal levels that exceed a minimum light level threshold, that fall below a maximum light level threshold, or that fall within an acceptable range of signal levels. If that number exceeds a predetermined number, the signal is determined to satisfy the signal quality criteria. Alternatively, the processor counts the number of peak signal levels falling outside the acceptable range of signal levels, and determines the signal quality criteria to be satisfied if that number is less than a predetermined number.

In other embodiments, the processor may count a number of individual elements of sensor 140 having signal values that exceed a minimum light level threshold, that fall below a maximum light level threshold, or that fall within an acceptable range of signal levels. If that number exceeds a predetermined number, the signal is determined to satisfy the signal quality criteria. Alternatively, the processor counts the number of individual elements of sensor 140 having signal levels falling outside the acceptable range of signal levels, and determines the signal quality criteria to be satisfied if that number is less than a predetermined number.

In other embodiments, the signal quality criteria may be defined as a number of peak signal levels that exceed a background signal level by some predetermined value. In such embodiments the processor analyzes the signal from the sensor to determine a background signal level. The background signal level may be, for example, the signal level at a point falling halfway in between two consecutive peaks $d_{mn}$ as illustrated in FIG. 2. Alternatively, the background signal may be an average signal level over a region of points falling between consecutive peaks, or an average signal level over plurality of such points or regions.

Having determined a background signal level, in embodiments the processor counts the number of peak signal levels that exceed the background signal level by a predetermined value. If that number is not less than a predetermined number, the signal is determined to satisfy the signal quality criteria. Alternatively, the processor counts the number of peak signal levels that do not exceed the background level by the predetermined threshold, and determines the signal quality criteria to be satisfied if that number is less than a predetermined number.

In other embodiments, once the background level is determined the processor may determine a signal-to-noise ratio—the peak signal level divided by the background level—for each peak signal level. Alternatively, signal-to-noise ratio may be determined for each of a subset of the peak signal levels (such as a subset of peak signal levels corresponding to a column or row of the lenslet array or corresponding to a region of particular interest in the patient's eye). The processor counts the number of peak signal levels having signal-to-noise ratios that exceed a predetermined signal-to-noise threshold. If that number is not less than a predetermined number, the signal is determined to satisfy the signal quality criteria. Alternatively, the processor counts the number of peak signal levels having signal-to-noise ratios that do not exceed a predetermined signal-to-noise threshold, and determines the signal quality criteria to be satisfied if that number is less than a predetermined number.

In still other embodiments, the signal quality criterion may be based upon an analysis of a histogram of the signal levels corresponding to each of the individual sensor elements. From FIG. 3, which is an image of the aberrometer detector output for a normal patient's eye, it should be apparent that a plot of such a histogram for such an image should feature two prominent histogram peaks. A first histogram peak containing relatively low signal values corresponds to the sensor elements recording background levels or near-background levels of signal. A second histogram peak containing points of higher signal value corresponds to the dots in the image of the aberrometer detector output. In contrast, in a histogram based upon the image of FIG. 4 (the aberrometer detector output for a cataract patient's eye), the histogram peak containing higher-signal elements will be smaller, since there are fewer high-signal dots in that image. As the power level of the light source 110 is increased, more dots will appear in the central region of the image of the cataract patient's eye, and consequently the histogram peak containing higher-signal elements will grow. Thus, in embodiments, the signal level criteria may be a predetermined minimum number of detector element output signal levels falling within the second histogram peak. The processor determines the signal quality criteria to be satisfied if the number of signal levels falling within the second histogram peak exceeds the predetermined minimum value.

In other embodiments, the signal quality criteria may be based upon a spatial Fourier transform of the signal from sensor 140. The Fourier transform of the signal may be a two-dimensional Fourier transform of the entire signal or a portion of the signal. Alternatively, it may be a one-dimension Fourier transform of the entire signal or a portion of the signal, such as the signal corresponding to a single row of sensor elements. For an adequate signal like that of FIG. 3, the Fourier transform of the signal will be dominated by the spatial frequency corresponding to the spacing between dots (and integer multiples of that frequency). For a signal like that of FIG. 4, which is compromised by opacification in the patient's eye, the decrease in signal levels in the center of the image diminishes the signal-to-noise ratio in the Fourier transform. In an embodiment in which the signal quality criteria are based upon the Fourier transform, the processor may determine the signal quality to be adequate by determining whether a signal-to-noise ratio of the Fourier transform exceeds some predefined threshold. The signal-to-noise ratio may be determined across the entire spectrum, across some sub-set or span of the spectrum, or at a single frequency or set of frequencies. In embodiments, the Fourier transform is filtered before the signal-to-noise ratio is determined. For example, the Fourier transform may be filtered to remove the DC component and/or extreme low frequency components.

In other embodiments, the signal quality criteria may be based upon an analysis of the center positions of the peaks (dots) in the image of the aberrometer detector output as determined by centroid analysis or any other technique used with Hartmann-Shack aberrometers. In such embodiments the processor determines the center positions of at least a subset of the peaks (dots), for example by centroid analysis, a curve-fitting algorithm, or other suitable techniques. An algorithm employed to determine the center position of a peak can, in some embodiments, return an uncertainty in center position (including an uncertainty in the x-dimension, in the y-dimension, or both) that is a measure of the accuracy with which the center position is determined. In such embodiments, the processor may count the number of peaks having positions that are determined with an uncertainty smaller than a predefined maximum acceptable uncertainty. If that number exceeds a predetermined number, the signal is determined to satisfy the signal quality criteria. Alternatively, the processor counts the number of peaks having positions that are determined with an uncertainty greater than a predefined maximum acceptable uncertainty, and determines the signal quality criteria to be satisfied if that number is less than a predetermined number.

In still further embodiments, when analyzing compromised data such as that of FIG. 4, the algorithm used to determine the center positions may simply fail to converge on any center position at all for dots in the low-signal region of the image. The algorithm may return a nonsense value or an error indicating that the algorithm failed to find a center position. In such embodiments, the processor may determine whether the signal detection criteria are satisfied by counting a number of center positions successfully returned by the algorithms for finding center positions. In such embodiments, the selection criteria are satisfied when the number of successfully determined center positions exceeds a predefined threshold.

Setting the Power Level.

As noted above, the processor 510 sets a power level of the aberrometer light source 110, for example in steps 610 and steps 660 of FIG. 6, or steps 710 and 760 of FIG. 7. Any suitable technique for automatically setting the power level of the aberrometer light source may be employed with the systems and methods of the present invention. In particular, embodiments of the invention include any combination of a technique for automatically setting the power level (including, but not limited to, those described below) with a technique for collecting and processing a signal representing reflected light from the patient's eye to determine whether the signal meets signal quality criteria (including, but not limited to, those described above).

In embodiments, the power level of the light source is set by setting a power control signal controlling the light source. Generally, the power control signal may be a current or voltage that can be set by a signal controlled by the processor 510. Any technique for controlling a light source via a current or a voltage can be used. For example, if the light source is a diode laser, its output power may be controlled by setting its operating current. If the light source is a lamp, its power may be controlled by setting a discharge voltage. In embodiments in which the light source is a laser driven by a pump source, setting the power level of the light source can be achieved by setting the power level of the pump. In still other embodiments, the light source may be a superluminescent LED (SLED), whose power is controlled by an applied control voltage or control current.

In embodiments, the light source is a pulsed laser and setting the power level of the light is achieved by pulse-width modulation. In such embodiments, the processor controls a pulse width of a control signal that is used to drive the light source. In pulse-width modulation, the output power of the light source is effectively increased by increasing the duty cycle—the percentage of a pulse duration for which the light source is on—of a pulsed light source. In embodiments using pulse-width modulation, the peak power output may be constant while the average power output varies with the pulse width.

In embodiments, the power level of the light source may be set by including an electronically controllable variable filter anywhere in the beam path. Such a variable filter may include a filter having a variable optical density (either continuously or stepwise variable). Alternatively the filter may comprise a polarization rotator followed by a polarizer. In other embodiments, a device such as a noise-eater or other amplitude modulator with an electronically settable output level may be employed anywhere in the beam path to set the power level of the light source. Additionally, in order to protect against setting the power level high enough to endanger the patient, the processor may be programmed not to exceed a maximum power level setting. In some embodiments, the light source itself is designed with a maximum power output low enough that a patient is not at risk of injury even at that maximum power output.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method comprising:
   setting automatically a first power level of light emitted by a light source;
   illuminating a retina of a patient with the light emitted by the light source;
   receiving, at a sensor, light reflected from the retina of the patient;
   providing a signal based upon the received light;
   determining whether the signal meets one or more signal quality criteria;
   setting automatically a second power level of light emitted by the light source in response to the determining whether the signal meets one or more signal quality criteria; and
   repeating illuminating, receiving, providing, and determining
   wherein determining whether the signal meets one or more signal quality criteria comprises:
   identifying a plurality of peak signal levels within the signal;
   determining a number of peak signal levels that are not less than a first predetermined value; and
   determining whether the number is not less than a redetermined number.

2. The method of claim 1, wherein repeating further comprises repeating until the signal meets the one or more signal quality criteria.

3. The method of claim 1, wherein determining whether the signal meets one or more signal quality criteria further comprises:
   identifying a background signal level, wherein the first predetermined value is a predetermined value by which the peak signal level exceeds the background level;
   and the step of determining a number of peak signal levels comprises determining a number of peak signal levels that exceed the background signal level by at least a predetermined value.

4. The method of claim 1, wherein
   the step of determining a number of peak signal levels comprises determining a number of peak signal levels that fall between a first predetermined value and a second predetermined value.

5. The method of claim 1, wherein determining whether the signal meets one or more signal quality criteria further comprises:
   identifying a background signal level;
   determining, for each of the plurality of peak signal levels, a signal-to-noise ratio;
   determining a number of signal-to-noise ratios that are not less than a predetermined value.

6. A method comprising:
   setting automatically a first power level of light emitted by a light source;
   illuminating a retina of a patient with the light emitted by the light source;
   receiving, at a sensor, light reflected from the retina of the patient;
   providing a signal based upon the received light;
   determining whether the signal meets one or more signal quality criteria;
   setting automatically a second power level of light emitted by the light source in response to the determining whether the signal meets one or more signal quality criteria; and
   repeating illuminating, receiving, providing, and determining wherein the signal comprises a plurality of signal levels, and
   wherein determining whether the signal meets one or more signal quality criteria further comprises:
   generating a histogram of at least a portion of the plurality of signal levels;
   identifying, in the histogram, a peak corresponding to a subset of the plurality of the signal levels comprising signal levels distinguishable from a background signal level; and
   determining whether a number of signal levels in the peak is not less than a predetermined value.

7. A method comprising:
   setting automatically a first power level of light emitted by a light source;
   illuminating a retina of a patient with the light emitted by the light source;
   receiving, at a sensor, light reflected from the retina of the patient;
   providing a signal based upon the received light;
   determining whether the signal meets one or more signal quality criteria;
   setting automatically a second power level of light emitted by the light source in response to the determining whether the signal meets one or more signal quality criteria; and
   repeating illuminating, receiving, providing, and determining
   wherein:
   the sensor comprises a plurality of elements; and
   the signal comprises a plurality of signal levels, each signal level corresponding to one of the plurality of elements of the sensor; and wherein determining whether the signal meets one or more signal quality criteria further comprises:
   determining, for each of the plurality of sensor elements, whether a signal at the sensor element is saturated;
   determining a number of sensor elements at which the signal at the sensor element is saturated; and
   determining whether the number is not greater than a predetermined number.

8. The method of claim 1, wherein determining whether the signal meets one or more signal quality criteria further comprises:
   generating a Fourier transform of at least a portion of the signal;
   determining a signal-to-noise ratio of at least a portion of the Fourier transform of the signal; and
   determining whether the signal-to-noise ratio is not less than a predetermined value.

9. The method of claim 1, wherein:
the sensor further comprises an array of sensor elements;
receiving further comprises receiving at the array of sensor elements light reflected from the retina of the patient through an array of lenslets; and
providing the signal further comprises providing a signal indicative of the optical power received at each of the sensor elements of the array of sensor elements.

10. The method of claim 9, wherein determining whether the signal meets one or more signal quality criteria further comprises:
determining a plurality of center positions in the signal, each center position corresponding to one of the lenslets in the array of lenslets;
determining an uncertainty in the center position for each of the plurality of center positions;
determining a number of center positions having uncertainties that are not greater than a predetermined uncertainty value; and
determining whether the number is not less than a predetermined number.

11. The method of claim 1, wherein setting the power level of the light emitted by the light source comprises setting a power control signal of the light source.

12. The method of claim 11, wherein setting the power control signal of the light source comprises setting the power control signal of the light source by pulse-width modulation.

13. The method of claim 1, wherein setting the power level of the light emitted by the light source comprises setting the attenuation of a filter in a beam path of the light emitted by the light source.

14. The method of claim 1, further comprising:
selecting an operating power based upon the signal quality criteria.

15. An apparatus comprising:
a light source adapted to illuminate a patient's retina;
a sensor adapted to receive light reflected from the patient's retina and to provide a signal based upon the received light; and
a processor coupled to the sensor and adapted to:
set a first power level of light emitted by the light source;
receive the signal provided by the sensor;
process the signal to determine whether the signal meets one or more signal quality criteria;
set a second power level of light emitted by the light source in response to determining whether the signal meets one or more signal criteria; and
repeat receiving the signal and processing the signal
wherein the processor is further adapted to:
identify a plurality of peak signal levels within the signal;
determine a number of peak signal levels that are not less than a first predetermined value; and
determine whether the number is not less than a predetermined number.

16. The apparatus of claim 15, wherein the processor is further adapted to repeat receiving the signal and processing the signal until the signal meets the one or more signal quality criteria.

17. The apparatus of claim 15, wherein the processor is further adapted to:
identify a background signal level, wherein the first predetermined value is a predetermined value by which the peak signal level exceeds the background level, and wherein the adaptation of the processor to determine a number of peak signal levels comprises the processor being adapted to determine a number of peak signal levels that exceed the background signal level by at least a predetermined value.

18. The apparatus of claim 15, wherein
the adaptation of the processor to determine a number of peak signal levels comprises the processor being adapted to determine a number of peak signal levels that fall between a first predetermined value and a second predetermined value.

19. The apparatus of claim 15, wherein the processor is further adapted to:
identify a background signal level;
determine, for each of the plurality of peak signal levels, a signal-to-noise ratio;
determine a number of signal-to-noise ratios that are not less than a predetermined value; and
determine whether the number is not less than a predetermined number.

20. An apparatus comprising:
a light source adapted to illuminate a patient's retina;
a sensor adapted to receive light reflected from the patient's retina and to provide a signal based upon the received light; and
a processor coupled to the sensor and adapted to:
set a first power level of light emitted by the light source;
receive the signal provided by the sensor;
process the signal to determine whether the signal meets one or more signal quality criteria;
set a second power level of light emitted by the light source in response to determining whether the signal meets one or more signal criteria; and
repeat receiving the signal and processing the signal wherein the signal comprises a plurality of signal levels, and wherein the processor is further adapted to:
generate a histogram of at least a portion of the plurality of signal levels;
identify, in the histogram, a peak corresponding to a subset of the plurality of the signal levels comprising signal levels distinguishable from a background signal level; and
determine whether a number of signal levels in the peak is not less than a predetermined value.

21. An apparatus comprising:
a light source adapted to illuminate a patient's retina;
a sensor adapted to receive light reflected from the patient's retina and to provide a signal based upon the received light; and
a processor coupled to the sensor and adapted to:
set a first power level of light emitted by the light source;
receive the signal provided by the sensor;
process the signal to determine whether the signal meets one or more signal quality criteria;
set a second power level of light emitted by the light source in response to determining whether the signal meets one or more signal criteria; and repeat receiving the signal and processing the signal wherein:
the sensor comprises a plurality of elements; and
the signal comprises a plurality of signal levels, each signal level corresponding to one of the plurality of elements of the sensor; and wherein the processor is further adapted to:
determine, for each of the plurality of sensor elements, whether a signal at the sensor element is saturated;
determine a number of sensor elements at which the signal at the sensor element is saturated; and determine whether the number is not greater than a predetermined number.

22. The apparatus of claim 15, wherein the processor is further adapted to:
generate a Fourier transform of at least a portion of the signal;
determine a signal-to-noise ratio of at least a portion of the Fourier transform of the signal; and
determine whether the signal-to-noise ratio is not less than a predetermined value.

23. The apparatus of claim 15, further comprising an array of lenslets, wherein:
the sensor comprises an array of sensor elements;
the sensor is further adapted to receive the light reflected from the patient's retina through the array of lenslets; and
the signal based upon the received light is indicative of the optical power received at each of the sensor elements of the array of sensor elements.

24. The apparatus of claim 23, wherein the processor is further adapted to:
determine a plurality of center positions in the signal, each center position corresponding to one of the lenslets in the array of lenslets;
determine an uncertainty in the center position for each of the plurality of center positions;
determine a number of center positions having uncertainties that are not greater than a predetermined uncertainty value; and
determine whether the number is not less than a predetermined number.

25. The apparatus of claim 15, wherein the processor is further adapted to set a power control signal of the light source.

26. The apparatus of claim 25, wherein the processor is further adapted to set the power control signal of the light source by pulse-width modulation.

27. The apparatus of claim 15, the apparatus further comprising a light attenuation filter disposed in a beam path of the light emitted by the light source, wherein the processor is further adapted to set an attenuation of the light attenuation filter.

28. The apparatus of claim 15, wherein the processor is further adapted to select an operating power based upon the signal quality criteria.

* * * * *